US012584912B2

(12) United States Patent
Öztürk et al.

(10) Patent No.: US 12,584,912 B2
(45) Date of Patent: Mar. 24, 2026

(54) IMMUNOCHROMATOGRAPHIC TEST STRIP

(71) Applicant: TUBITAK, Ankara (TR)

(72) Inventors: Tarik Öztürk, Kocaeli (TR); Mediha Esra Yayla, Kocaeli (TR)

(73) Assignee: TUBITAK, Ankara (TR)

( * ) Notice: Subject to any disclaimer, the term of this patent is extended or adjusted under 35 U.S.C. 154(b) by 1429 days.

(21) Appl. No.: 16/759,392

(22) PCT Filed: Oct. 26, 2018

(86) PCT No.: PCT/IB2018/058382
§ 371 (c)(1),
(2) Date: Apr. 27, 2020

(87) PCT Pub. No.: WO2019/082145
PCT Pub. Date: May 2, 2019

(65) Prior Publication Data
US 2020/0326336 A1 Oct. 15, 2020

(30) Foreign Application Priority Data
Oct. 27, 2017 (TR) ................................. 2017/16609

(51) Int. Cl.
*G01N 33/543* (2006.01)

(52) U.S. Cl.
CPC . *G01N 33/54388* (2021.08); *G01N 33/54387* (2021.08)

(58) Field of Classification Search
CPC ....... G01N 33/54386; G01N 33/54387; G01N 33/54388; G01N 33/558; G01N 33/54389;

(Continued)

(56) References Cited

U.S. PATENT DOCUMENTS

| | | | |
|---|---|---|---|
| 7,476,533 B2 * | 1/2009 | Meathrel | G01N 33/54366 436/514 |
| 7,829,347 B2 * | 11/2010 | Song | G01N 33/521 436/514 |

(Continued)

FOREIGN PATENT DOCUMENTS

| | | |
|---|---|---|
| WO | 2013/115478 | 8/2013 |
| WO | 2016/178013 | 11/2016 |
| WO | 2018/049272 | 3/2018 |

OTHER PUBLICATIONS

Fang et al ("Barcode lateral flow immunochromatographic strip for prostate acid phosphatase determination", Journal of Pharmaceutical and Biomedical Analysis, 56 (2011), 1035-1040) (Year: 2011).*

(Continued)

*Primary Examiner* — Christopher L Chin
(74) *Attorney, Agent, or Firm* — Bayramoglu Law Offices LLC

(57) ABSTRACT

The present invention relates to an immunochromatographic test strip (1) which can be encoded such that the test result cannot be understood by the user who performs the test. The test strip (1) subject of invention, includes at least one sample pad (2) in which the samples are loaded, at least one conjugate pad (3) having analyte-specific labeled antibodies present in the sample, at least one membrane (4) wherein the antibodies bound or unbound to the analyte moves forward and at least one absorption pad (5) providing movement of the sample and a two-dimensional barcode (6) on the membrane (4) that provides the authorities to interpret the results and avoids one who takes test image after test so that the test taker does not immediately understand the test result.

11 Claims, 1 Drawing Sheet

Figure 1:
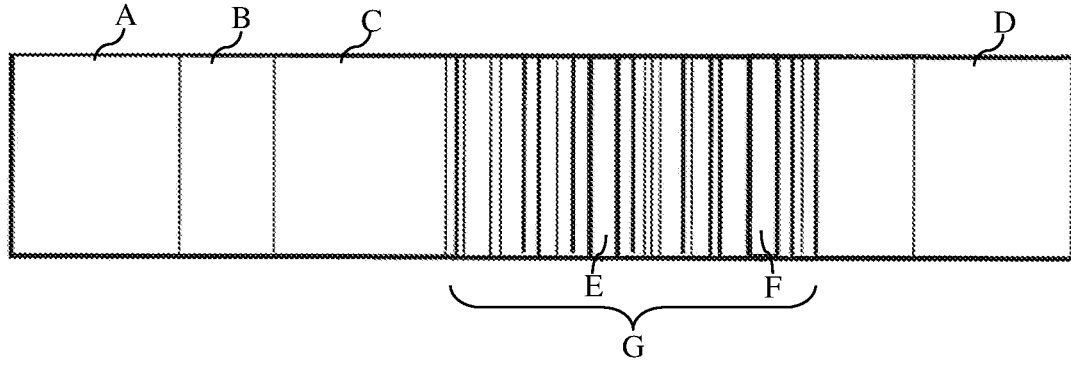

(58) Field of Classification Search
    CPC .......... G01N 2035/00752; G01N 2035/00772;
                                B01L 2300/0825; B01L 2300/021
    USPC ....... 422/400, 401, 420, 421, 425, 426, 430;
                                435/287.7, 287.9, 970, 805, 810;
                                436/169, 170, 514, 518, 530, 810
    See application file for complete search history.

(56)                  References Cited

U.S. PATENT DOCUMENTS

| | | | | |
|---|---|---|---|---|
| 8,399,261 | B2 * | 3/2013 | Kabir ..................... | G01N 31/22 |
| | | | | 436/514 |
| 12,352,747 | B2 | 7/2025 | Armbruster | |
| 2003/0124738 | A1 * | 7/2003 | Crosby ............ | G01N 33/54388 |
| | | | | 436/514 |
| 2006/0240568 | A1 | 10/2006 | Petruno et al. | |
| 2016/0232421 | A1 | 8/2016 | Decker et al. | |

OTHER PUBLICATIONS

Thomas F. Scherr et al: "An embedded barcode for "connected" malaria rapid diagnostic tests", Lab on a Chip, vol. 17, No. 7, Feb. 22, 2017 (Feb. 22, 2017), pp. 1314-1322, XP055552148, p. 1315, left-hand column, last line; figure 1.
Ioannis N. Katis et al: "Paper-based colorimetric enzyme linked immunosorbent assay fabricated by laser induced forward transfer", Biomicrofluidics, vol. 8, No. 3, 2014, p. 036502, XP055552225, p. 6, lines 7-8; figure 4.
Identify Direct Ltd, Beginners Guide to 2-D Barcodes, ID Identify Direct, pp. 1-20.

* cited by examiner

IMMUNOCHROMATOGRAPHIC TEST STRIP

TECHNICAL FIELD

The present invention relates to an immunochromatographic test strip which can be encoded such that test result cannot be understood by the user who performs the test.

PRIOR ART

The use of test strips began in the 1980s and since then test strips have found use in the detection of molecules such as antigen, antibody and mycotoxin. The market of test strips reached 967.6 million dollars in 2015. It is expected that the market of horizontal flow test strips will reach 6.78 billion dollars in 2020 and find wide use especially in the fields of medicine, food and environment.

Immunochromatographic test strips combine bio-identification probes with chromatography. These tests are one-step, fast, device-independent and user-friendly. Immunochromatographic test strips are highly sensitive due to their chromatographic separation and do not interact with other compounds.

The immunochromatographic test strip is composed of at least two sections, one control and one test line. The test region contains the analyte (s)-specific antibodies while the control region contains the analyte (s)-secondary antibodies capable of retaining the specific antibodies.

Immunochromatographic test strips generally come from four main parts. These sections are; sample pad, conjugated antibody pad, nitrocellulose membrane and absorption pad. Analyte-containing liquid dropped on sample pad is first transported to the conjugated antibody pad of the test strip by a liquid absorbing pad. In the conjugated antibody pad part, there are labelled target specific antibodies. Those labelled antibodies bind specifically to the analyte. In the conjugated antibody pad the analyte bound and unbound antibodies begin to migrate from the conjugated antibody pad to the nitrocellulose membrane. When the analyte-bound antibodies arrive on the nitrocellulose membrane, they are retained by immobilized analyte-specific antibodies as a line on the nitrocellulose, thereby staining the test strip in this region. Analyte unbound antibodies are retained by the secondary antibodies present in the control region to stain the control band.

A top view of an example of the immunochromatographic test strip in the known state of the art is shown in FIG. 1. The said immunochromatographic test strip contains a sample pad (A) loaded with the specimens to be tested on it, a conjugate pad (B) containing analytes-specific labelled antibodies in the specimen, a membrane (C) where all of the antibodies bound and unbound to the analyte advances from conjugated pad (B) to it and an absorbent pad (D) that allows sample to travel on the strip. Membrane (C) includes test region (E) which allows for the capture of the labeled antibodies which are bound to the analyte, a control region (F) which allows for the capture of all antibodies that bound or not bound to the analyte, and preferably a barcode region (G) which allows for the display of a different code according to the test result for digitizing process of test feature and result. In this immunochromatographic test strip shown in FIG. 1, the labeled antibodies have to pass through the test site first and then through the control site; and since all the antibodies have to pass through the test and control sites the test result can be easily understood by the user who has made the test.

In the case of immunochromatographic test strips known in the state of the art, it is mandatory to place the test antibodies in the front and control antibodies in the back as the control antibodies which are secondary antibodies present in the control region bind all antibodies bound or not bound to the analyte. This requirement makes the test results easy to understand by the user.

In some cases, understanding the results of immunochromatographic test strips by the user may be objectionable because of manipulation of results or trying to hide the results. Tests that require food inspections or legal liability can lead to a variety of problems as the result can be understood by the testing user.

For this reason, there are needed immunochromatographic test strips that can be encoded so that the user who makes the test cannot understand the test result in the known state of the art.

The U.S. patent document no U.S. Pat. No. 3,907,503 mentions a test system containing a barcode and used to analyze a chemical component. This system reads the test reagents and preferably the calibration data with the barcode on the test strip and programs itself. However, the strip used in this system is not an immunochromatographic test strip but a chemical analysis strip. In the patent document, a special encryption is also not used which makes the test result unknown to the user.

The U.S. patent document no U.S. Pat. No. 6,036,092 mentions a test system comprising a barcode used to analyze a component. With this system, the data can be encrypted. The system also mentions the use of the immunochromatographic test strip but does not mention the encoding of the immunochromatographic test strip so that the user does not understand the test result.

BRIEF DESCRIPTION OF THE INVENTION

The aim of the present invention is to realize an immunochromatographic test strip that can be encoded so that it cannot be understood by the user who performs the test.

Another aim of the present invention is to carry out an immunochromatographic test strip which allows the result of the performed test to be understood at an imaging center.

DETAILED DESCRIPTION OF THE INVENTION

Figure 2:
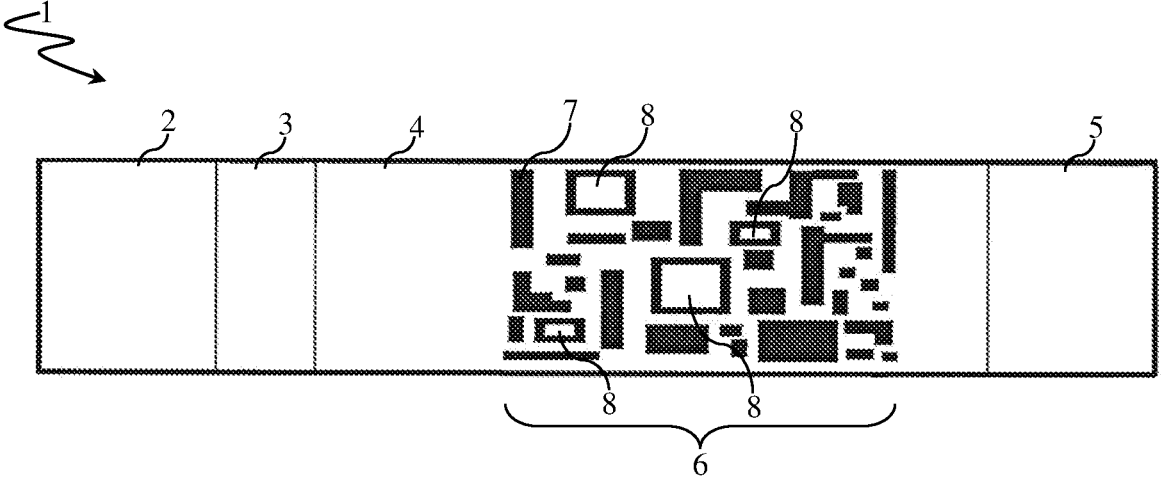

"An Immunochromatographic Test Strip" performed to achieve the purpose of this invention is shown in the attached figures, from these figures;

FIG. 1. Top view of an immunochromatographic test strip according to the known state of the art;

FIG. 2. A top view of an immunochromatographic test strip according to the present invention.

The parts in the figures are numbered individually and the correspondences of these numbers are given below.

1. Immunochromatographic test strip
2. Sample pad
3. Conjugated pad
4. Membrane
5. Absorption pad
6. Barcode
7. Content fixed region
8. Content-varying region according to the test result
A: sample pad of an immunochromatographic test strip according to the known state of the art
B: conjugated pad of an immunochromatographic test strip according to the state of the art C: membrane of an immunochromatographic test strip according to the state of the art D: absorption pad of an immunochromatographic test strip according to the known state of the art.

E: test region located on the membrane of an immunochromatographic test strip according to the state of the art F: the control region located on the membrane of an immunochromatographic test strip according to the state of the art G: a barcode region located on the membrane of an immunochromatographic test strip according to the state of the art The immunochromatographic test strip (1) includes at least one sample pad (2) in which the samples are loaded, at least one conjugate pad (3) having analytes-specifically labeled antibodies present in the sample, wherein the antibodies bound or unbound the analyte advances at least one membrane (4) and at least one absorption pad (5) providing the advancement of the sample.

In the immunochromatographic test strip (1) subject of the invention, the membrane (4) comprises a two-dimensional barcode (6). The barcode (6) comprises at least one content fixed zone (7) and several content-varying regions according to the test result (8), content-varying region according to test result (8) are located on the barcode (6) in such a way that they do not come in succession, in other words, they do not come back consecutively to the axis through which the immunochromatographic test strip (1) extends. After the test is performed at this point, the image of the barcode (6) is taken and the test result can be interpreted in the direction of the content-varying region (8). The user who performed the test by this means is unable to comment on the test results.

In the preferred application of the invention, the barcode (6) comprises at least two content-varying regions (8).

In one application of the invention, the immunochromatographic test strip (1) provides for the analysis of more than one analyte at the same time. In this application of the invention, the analyte-specific antibodies to be analyzed are placed in content-varying regions (8) parallel to each other so as not to cross-react with each other.

In the preferred application of the invention, at least one part of the content-varying region according to test result (8) includes analyte-specific antibodies, also known as test antibodies, and all antibodies-specific secondary antibodies, also known as control antibodies.

The barcode (6), located in the immunochromatographic test strip (1) subject of the invention must be configured to give information of the location of the content-varying region according to the test results (8) and test antibodies of such regions (8) control antibodies or empty. In the preferred application of the invention, said information is embedded in a code contained in the barcode (6). In an alternative application of the invention, the said information is reached by querying an external database for an indicator on the barcode (6). In a derivative of this embodiment of the invention, the barcodes (6) of the different immunochromatographic test strips (1) contain a special marker of the barcodes (6).

In one application of the invention, the barcode (6) comprises more than one color. In this way, the shapes on which the barcode (6) is played can be determined by determining the shade of the colors on the barcode upon processing of colors and the deviations in the reflections.

In one application of the invention, the absorption pad (5) comprises a stain determined according to the diffusion coefficient analysis time. Said stain remains in the absorption pad (5) without dispersion when the flow direction is from the sample pad (2) to the absorption pad (5) but only when the flow of the sample stops, spreading over the test strip (1) all to estimate the time elapsed between the test and the taking of the image. Thus the tests that give positive results are made before time and the results are prevented from being used later.

In an alternative application of the invention, the stain may be located in any region after the barcode (6) on the membrane (4).

In an alternative application of the invention, the absorption pad (5) comprises at least one encapsulated chemical substance which is structured to remove or destroy the barcode (6) within a certain period of time after the test is carried out. In an alternative application of the invention, the encapsulated chemical substance may also be present in any region after the barcode (6) on the membrane (4).

In one application of the invention, at least one of the varying regions (8) according to the test result on the barcode (6) comprises an antibody or chemical indicator. Thus it can be determined whether the test is performed by the same user or by a substance from the same production line. Said indicator may be selected from blood group among blood sample, iron level or any indicator or indicator group which may differ between people. The indicator can be selected for food samples, for example, pH, sugar level, salt content, amino acid content, mineral content.

In one application of the invention, the barcode (6) contains three different colors placed on it. Thus the colors placed on the barcode (6) during the taking of the barcode image (6) serve as a calibration curve. Said color content is used to calculate the quantitative results in the case of quantitative results of the indicator or antibodies placed in the varying regions (8) according to the test result.

In one application of the invention, the barcode (6) has an internal image standard that allows the digitization of the image taken by a camera. This avoids the deviations that may occur due to shadows and reflections in images taken with the camera.

In an advantageous application of the invention, the barcode (6) images, for example, a mobile phone, are sent to remote servers via a smartphone. In this application of the present invention, in transmitting the images of the barcode (6), the image of the barcode (6) received from the mobile device camera is encrypted so that the images are separated from other images on the mobile device and manipulations on the images or visual images are executed, and an application transmitting to the remote server is executed on the mobile device. In one application of the invention, the application inserts the location and date tag in the barcode image (6) received via the camera.

In the immunochromatographic test strip (1), it is not possible to perceive the test result by the user performing the test by using the content-varying regions (8) according to the test result. It is possible to encrypt test results in many different ways. In the application in which the immunochromatographic test strip (1) contains four regions of content depending on the test result, it is possible to make 54 different coding combinations if these regions (8) are coded as control, blank and test, even assuming that the regions (8) remain fixed in shape and size. In addition, by changing the dimensions of the regions (8) and their positions on the barcode (6), the combination of codes can be further increased.

Around these basic concepts, it is possible to develop a wide variety of applications relating to the invention "An Immunochromatographic Test Strip", the invention not being limited to the examples described herein, it is exactly as specified in claims.

What is claimed is:

1. An immunochromatographic test strip to prevent an interpretation of test results by a user performing the immunochromatographic test, comprising:

at least one sample pad in which a sample is loaded;

at least one conjugate pad having analyte-specific labeled antibodies, that bind specifically to analytes present in the sample, and at least one membrane onto which the labeled antibodies, whether bound or unbound to the analyte, migrate from the conjugate pad;

at least one absorption pad providing advancement of the sample; and a two-dimensional barcode located on the membrane, the barcode comprising:

at least one content fixed zone comprising barcode content that does not vary according to a test result, and one or more content-varying regions comprising barcode content that varies according to the test result, wherein the content-varying regions are located on the barcode in such a way that they do not come in succession, at least one part of the content-varying regions comprises analyte specific antibodies, and all antibodies-specific secondary antibodies, and at least one of the content varying regions is empty.

2. The immunochromatographic test strip according to claim 1 wherein the barcode comprises at least two content-varying regions.

3. The immunochromatographic test strip according to claim 1 wherein the analyte-specific labeled antibodies are placed parallel to each other so as not to cross-react with each other.

4. The immunochromatographic test strip according to claim 1 wherein the two-dimensional barcode has an embedded code to give information of a location of the content-varying regions and test antibodies of the content-varying regions control antibodies or empty.

5. The immunochromatographic test strip according to claim 1 wherein the two-dimensional barcode has an indicator to reach information by querying an external database to give information of location of content-varying regions according to the test results and test antibodies of the content-varying regions control antibodies or empty.

6. The immunochromatographic test strip according to claim 1 wherein the two-dimensional barcode comprises more than one color.

7. The immunochromatographic test strip according to claim 1 wherein the absorption pad comprises a stain determined according to a diffusion coefficient analysis time.

8. The immunochromatographic test strip according to claim 1 wherein the membrane comprises a stain determined according to a diffusion coefficient analysis time between the barcode and the absorption pad.

9. The immunochromatographic test strip according to claim 1 characterized with wherein the absorption pad comprises at least one encapsulated chemical substance.

10. The immunochromatographic test strip according to claim 1 wherein the membrane which comprises at part between the barcode and the absorption pad at least one encapsulated chemical substance.

11. The immunochromatographic test strip according to claim 1 wherein the content-varying regions comprise an antibody or chemical indicator.

* * * * *